United States Patent [19]
Smyth

[11] Patent Number: 5,726,916
[45] Date of Patent: Mar. 10, 1998

[54] METHOD AND APPARATUS FOR DETERMINING OCULAR GAZE POINT OF REGARD AND FIXATION DURATION

[75] Inventor: Christopher C. Smyth, Fallston, Md.

[73] Assignee: The United States of America as represented by the Secretary of the Army, Washington, D.C.

[21] Appl. No.: 675,330

[22] Filed: Jun. 27, 1996

[51] Int. Cl.$^6$ .................................................. A61B 3/14
[52] U.S. Cl. ............................. 364/559; 364/516.444; 364/571.414; 364/559.444; 395/20; 351/210
[58] Field of Search ............... 364/559.444, 516.444, 364/571.414; 351/209, 211, 210, 212, 246; 340/825.19; 348/15; 345/7; 356/139.03; 395/20, 21

[56] References Cited

U.S. PATENT DOCUMENTS

| | | | |
|---|---|---|---|
| 5,386,258 | 1/1995 | Nagano | 354/400 |
| 5,410,376 | 4/1995 | Cornsweet et al. | 351/210 |
| 5,583,795 | 12/1996 | Smyth | 364/516.444 |
| 5,649,061 | 7/1997 | Smyth | 395/20 |

OTHER PUBLICATIONS

Adams, Charlotte (Mar. 1990), "If Looks Could Kill: The Eyes Have It", Military & Aerospace Electronics, pp. 35–37, Mar. 1990.

Monty, et al, "Eye Movements and Psychological Processes", Hillsdale, pp. 185–199, no date.

Calhoun et al., "Proceedings of the Human Factors Socciety 30th Annual Meeting" 1986.

Jacob, "What you see is what you get: the use of eye movements in human–computer interaction techniques", Naval Research Laboratory, 1989.

*Primary Examiner*—James P. Trammell
*Assistant Examiner*—Kamini S. Shah
*Attorney, Agent, or Firm*—Muzio B. Roberto; Paul S. Clohan

[57] ABSTRACT

A method and apparatus for determining ocular gaze point of regard and fixation duration utilizing Electrooculographic measurements and head position and orientation data. The Electrooculographic (EOG) potentials from an unipolar measuring configuration, are first amplified, filtered and digitized. A computation scheme based on the mathematical relation for the sum and difference potentials between opposing electrodes placed about the eye is then used to compute ocular orientation and amplifier gains and DC bias offset voltages. The sensor system of the invention may be embedded in a neoprene holder for a helmet mounted display; the holder fitting around the eyes like a set of goggles, is against the face well out of the way of the natural field of view. The invention is easily extended to the simultaneous tracking of both eyes thereby allowing the measurement of the optical convergence point in the user's three dimensional workspace either real or virtual. The invention can be used as an eyetracker to control computerized machinery by ocular gaze point of regard and fixation duration. For this reason, the invention has potential applications to the aviation cockpit during tasks demanding high visual and motor loading such as occur in low level helicopter flight.

6 Claims, 7 Drawing Sheets

METHOD AND APPARATUS FOR DETERMINING OCULAR GAZE POINT OF REGARD AND FIXATION DURATION

GOVERNMENTAL INTEREST

The invention described herein may be manufactured, used and licensed by or for the United States Government without payment to me of any royalty thereon.

CROSS-REFERENCE TO RELATED APPLICATIONS

The subject matter of this application is related to that disclosed in application Ser. No. 08/439,392 filed May 11, 1995, U.S. Pat. No. 5,649,061 Ser. No. 08/407,142 U.S. Pat. No. 5,583,795 filed Mar. 17, 1995, Ser. No. 08/675,329 filed Jun. 27, 1996, now allowed and Ser. No. 08/695,847 filed Aug. 9, 1996 now allowed.

TECHNICAL FIELD

The present invention relates to a method and apparatus for determining the ocular gaze point of regard and fixation duration of the human eye, from electrooculographic measurements. The invention has possible applications to such areas as measurement of ocular functions in human factors studies, as a tool for medical diagnosis of ocular functions, as an aid to the handicapped, or as an electronic safety net to detect performance degradation due to pilot incapacitation in piloted vehicles, and for human operator control of machines. Examples of machine control by ocular functions are:

1) Updating computer generated information displays;

2) Selecting panel switches and instruments;

3) Controlling the fidelity of computer generated imagery scene inserts in simulation;

4) Controlling the viewing direction of remotely located cameras;

5) Controlling the movement of tele-operated robotics platforms or vehicles;

6) Selecting display subareas for automated scene analysis in aided target recognition;

7) Designating a target from direct sight or from a sensor display; and

8) Weapon system pointing.

DESCRIPTION OF THE PRIOR ART

The existing technology for oculometers that perform similar functions is based on any of the following well established optical measuring techniques: pupil tracking, lumbus boundary, double punkenje image, corneal reflections or retinal image. Essentially, these techniques depend upon the optical measurement of reflected infrared light from the human eye, an approach which is more than thirty years old in concept. In its simplest form, an oculometer contains an infrared light source which is directed at the eye and the reflected light is imaged onto a charge-coupled device sensor array. The image of the eye is then electronically processed to determine the corneal reflection, the pupil centroid orientation, or both. These parameters are used to determine the angular location of the eye relative to the camera within a fair degree of accuracy. The technology is either head-mounted or mounted in a panel in front of the user.

The head mounted systems are awkward to wear. The accompanying optics used to illuminate and image the eye, are bulky and heavy, and induce neck and shoulder muscle fatigue. The infrared light source must be placed next to the eye; a filter shields the source, eye, and sensor from the ambient light. A semi-reflective mirror is placed within the field of view to reflect the image of the eye to the sensor array. The optical arrangement has a limited field of view usually no more than 20-degrees, and interferes with the visual field. The user must use limited eye movements coupled with excessive head movements to keep the eyes in view. The boresight established in calibration is easily perturbed by head movement or vibration induced disturbances in the head support system. In addition, adjustment difficulties may occur with individuals having a large nose bridge, deep lying eyes, bulging eyes, jutting eye lids, or other extreme deviations in facial structure.

These limitations become apparent when integrating the present technology with helmet mounted displays. Recent advances in display technology have produced extremely light weight helmet mounted displays comparable in size to bulky sunglasses. The eye relief distance is specified in millimeters and there is little room between the display and the eye for placing the infrared sources and fiber optics probes used with the present technology.

In contrast, the optics for the panel mounted system are mounted in front of the user and directed toward his face. The panel mounted system is limited to low ambient light levels and objects that the user may need to work with cannot be placed between his face and the optics. A servomechanism is used to keep the optics aligned on the user's eye, and the servomechanism adjustment is noticeable to users following head movement. Excessive head movements and interference of the optical path by facial features such as the user's nose are not tolerated. Modern developments in helmet mounted displays cannot be used with panel mounted oculometers.

The oculometers based on optical technology can be used to determine the angular location of the eye relative to the sensor array within a fair degree of accuracy. The measurement of head position and orientation for the head-mounted system allows the determination of eye position and orientation in the workspace, and therefore the computation of the eye point of regard. Similarly, the determination of the range from the sensor to the eye by either ultrasonic or image focusing allows the computation of eye point of regard for the panel system. The accuracy of the technology is roughly about one degree in practice. A lower limit appears to be about one-half degree; however, this may be due to the nature of the human vision process since this is about the size of the foveal.

One potential application of oculometers that has been investigated is the control of machines from visual displays by ocular functions. The oculometer is use to determine the location of the user's visual attention. The user may be looking over a display or scene to acquire task related information in preparation to initiating machine control. Some means is required for the subject to indicate that a particular display icon or scene feature has been selected by him for machine control. The length of the visual dwell time tends to be greater for display icons of interest. Dwell time less than 150 milliseconds are associated with icons not of interest; times longer than 250 milliseconds tend to be associated with icons of interest. However, the dwell time is a statistical process and the user usually confirms the selection with a consent motor response or waits for the selection to time out. For example, the user may perform a motor function in conjunction with a forced gaze at a selected item, by pressing a switch or speaking a voice command to an automatic speech recognizer.

The invention uses an alternative method employing electrooculographic measurements of the ocular function, a well established medical technique based upon the electrostatic properties of the human eye. The retinal is normally negatively charged relative to the corneal of the eye. This potential difference is constant for a given light adaptation without changes in light stimulation. The difference in electrostatic charge creates an electric dipole moment aligned along the optical axis; the resulting retinal resting potential generates a vast dipole electric field about the eyeball. The corresponding electrostatic field is fixed and rotates with the eye; however, the field induces electrical potentials on the surface of the skin covering the flesh surrounding the skull orbit (socket) of the eye. The potentials change with the eye rotation; the potential difference between skin surface electrodes placed on opposite sides of the orbit changes almost sinusoidally with rotation in the direction between the electrodes.

For technical reasons, the application of electrooculographic measurements to eyetrackers in which skin-surface electrodes located about the eye are used to infer viewing direction, has not been fully developed prior to this invention. The EOG potential, induced by the electrostatic dipole field associated with the intrinsic ocular retinal potential, varies widely with the individual. The potential difference between electrodes on the face above and below the eye is typically on the order of millivolts per degree of eye rotation. The past limitations of skin surface electrode measurements, the need for extensive skin surface and electrode preparation, electrode signal drift over time, and low signal amplitude in the millivolt range have limited the application of electrooculographics to clinical studies. However, recent improvements in electrode and amplifier technologies have removed the need for extensive preparation, and electrode signal drift is only a problem for extended application periods. Still changes in measured EOG potential can occur with the skin-surface electrodes shifting with changing facial expressions and with momentarily upper eye lid lag overshoot, eye blinks episodes, and facial fast muscle potentials. A far more severe limitation is that the strength of the retinal potential varies with changes in the light adaptation level and viewing conditions. The retinal potential is an intrinsic variable not readily measured; and the resulting changes in EOG potential without compensatory adjustments in gain, may saturate the corresponding instrumentation amplifiers used to measure the voltage.

These technical limitations have severely restricted the applications of electrooculographic measurements to eyetrackers in prior developments. For example, the literature reports on the use of a discrete eye-position recorder for control of a display by the handicapped which uses EOG measurements to determine when the user's gaze has moved from one matrix element to an adjacent one in a vertically arranged display format; the bias offset voltage of the recording amplifier is then reset so that the EOG signal measured is zero as long as that matrix element is being viewed.

SUMMARY OF THE INVENTION

The invention incorporates novel features to ensure the practical applications of electrooculographic (EOG) amplifiers used to measure the EOG potentials. The invention automatically adjusts the amplifier gains and bias voltages for the changes in retinal potential with light adaptation during viewing and for the drifts in electrode bias voltage.

In addition, the invention in a further embodiment, employs a photodiode to measure the ambient light facing the viewer and with this data and an expert knowledge of eye pupil diameter changes with light levels and the resulting light adaptation levels, accurately predict the changes in retinal potential. This result is used in computing the compensatory adjustments in amplifier gains and bias offset voltages.

The invention makes use of recent improvements in electrode and amplifier technologies which have removed the need for extensive skin-surface preparation, and as a result, electrode signal drift is only a problem for extended application periods.

The invention uses a three dimensional model of the optical process to compute the viewing direction from the optical axis; the ocular angular offsets determined from the EOG potentials are used to determine the angular orientation of the ocular optical axis which is naturally aligned with the electrostatic dipole of the eye.

The invention uses an expert system based on an established knowledge about the visual process to compute eye fixations from the viewing directions and the head position and orientation measurements. The eye gaze point of regard and fixation duration are then computed from the fixation patterns.

The invention is easily extended to the simultaneous tracking of both eyes thereby allowing the measurement of the viewing convergence point in the user's three dimensional workspace either real or virtual.

The invention when used with a video display, is auto-calibrating since the user can quickly and accurately exercise a calibration procedure that correlates visual fixation position with line of sight.

The invention can be used as an eyetracker to control computerized machinery by ocular gaze point of regard and fixation duration. The invention determines the ocular fixation dwell time; this parameter may be used to pre-select a display element causing it to be illuminated as feedback to the user. The user confirms the selection with a consent motor response or waits for the selection to time out. The ocular fixation dwell time tends to be longer for display element of interest.

The invention can sample the electrooculogram at a rate high enough for the accurate determination of the duration of the eye blink and the onset of a visual fixation. This is true because the EOG is a continuous analog signal. The endogenous eye blink duration is used in the human factors' analysis of workload as a measure of the visual attention to a task. Short closure durations and low blink rates are associated with visual attention. On the other hand, increased blink rates and longer blink durations occur with the buildup of operator fatigue. The differences in the blink durations for these conditions are commonly on the order of milliseconds. This resolution is difficult to measure at the video refresh rates that are attained with optical oculometers using a CCD (charge coupled device) arrays for image collection and analysis. Similarly, because of the high sampling rate, the invention measures the start of visual fixation with sufficient accuracy to align the event with the measurements of the cerebral potential. This feature is of interest for applications that utilize the relations between brain waves and eye movements.

The invention can track eye movements over nearly the full extend of the human visual field. This is true, because the goggles with the measuring electrodes lies fairly flat against the face and obstruct only the far edges of the visual field. This is in contrast to oculometers using optical technology, where the tracking is limited to the central vision field by the optical design.

For this reason, the invention can be used as a component of an oculometric system to complement the tracking range of an oculometer based on optical technology. As mentioned above, the optical oculometer is limited to the central field of view used to image the eye, while the invention tracks viewing beyond the central region. In this way, the design expands the tracking to nearly the full extend of the human visual field. Further, the design can perform automated intermittent calibration to account for long term drift of the constants in the equations for the EOG potentials and the viewing relations. This is done by the optical oculometer when the viewer looks within the central tracking field.

The advantages of the invention over the existing technology are the low cost, slight bulk, light weight, high sampling rate, independence of facial geometry, ease of application and calibration, and wide field of view. These advantages make the invention particularly attractive for measuring ocular functions with virtual image displays such as helmet mounted displays (HMD's) and night vision goggles. The Electrooculographic sensor system of the invention may be embedded in the neoprene holder for a helmet mounted display; the holder fitting around the eyes like a set of goggles, is against the face well out of the way of the natural field of view. For this reason, the invention has potential applications to the aviation cockpit during those tasks demanding high visual and motor loading such as occur in low level, nighttime helicopter flight.

BRIEF DESCRIPTION OF THE DRAWINGS

Other objects and advantages of the invention will become apparent upon reading the following detailed description and upon reference to the drawings, in which.

DETAILED DESCRIPTION OF THE PREFERRED EMBODIMENTS

Figure 1:
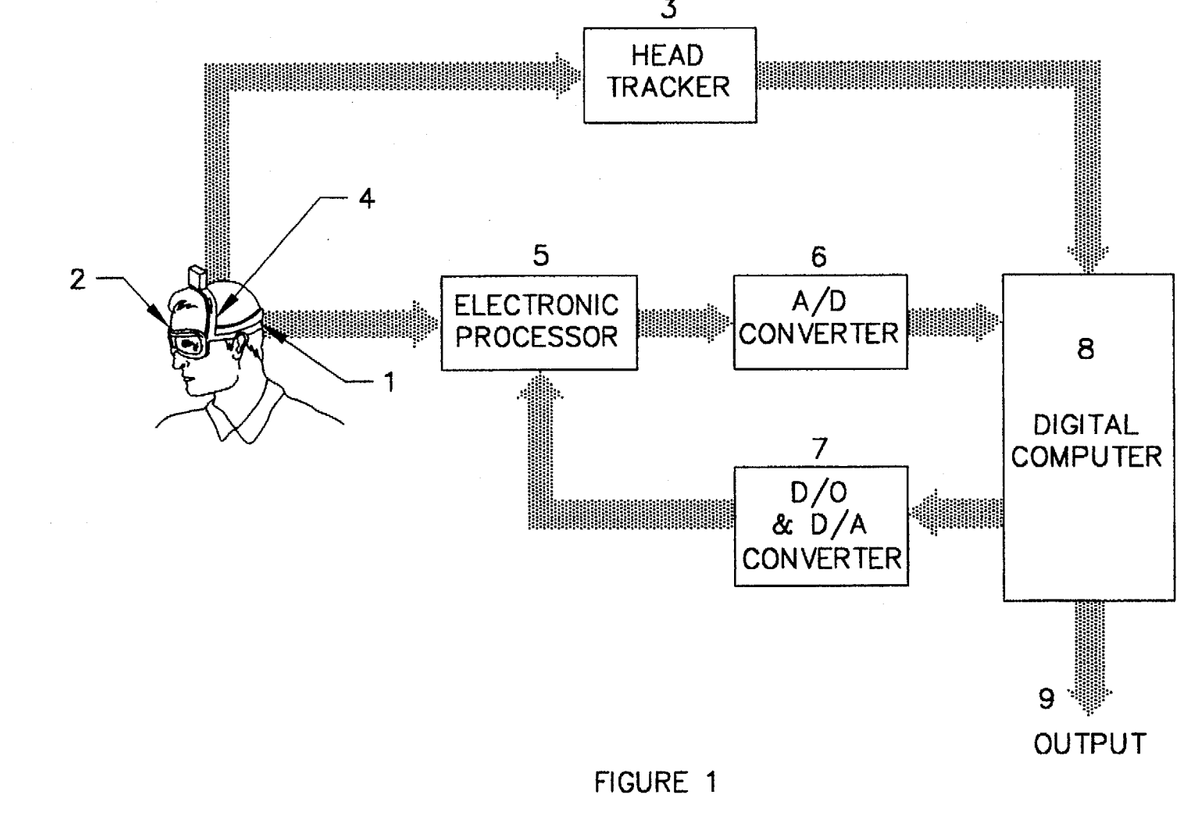
FIG. 1 depicts a block diagram for the hardware components of the invention.

FIG. 1 shows a schematic of the hardware components of the invention. The user of the invention is wearing a headset 1 with goggles 2 holding electrooculographic (EOG) electrode sensors 4, and supporting a head tracker 3. The analog electrical potentials measured by the EOG skin-surface electrode sensors 4 are amplified and filtered by the electronic processor 5. The analog electrical output of processor 5 is digitized by the analog-to-digital converter 6, the multiplexed output of which is a digital electrical input to the digital computer 8. The head position and orientation sensor 3 provides a digital electrical input to the digital computer 8. The computer 8 outputs an digital electrical signal which is converted by the digital-to-analog converter and digital output device 7 into electrical control signals for the programmable amplifiers of the processor 5. The digital electrical output 9 of the computer 8 is the computed gaze point of regard and fixation duration.

Figure 2:
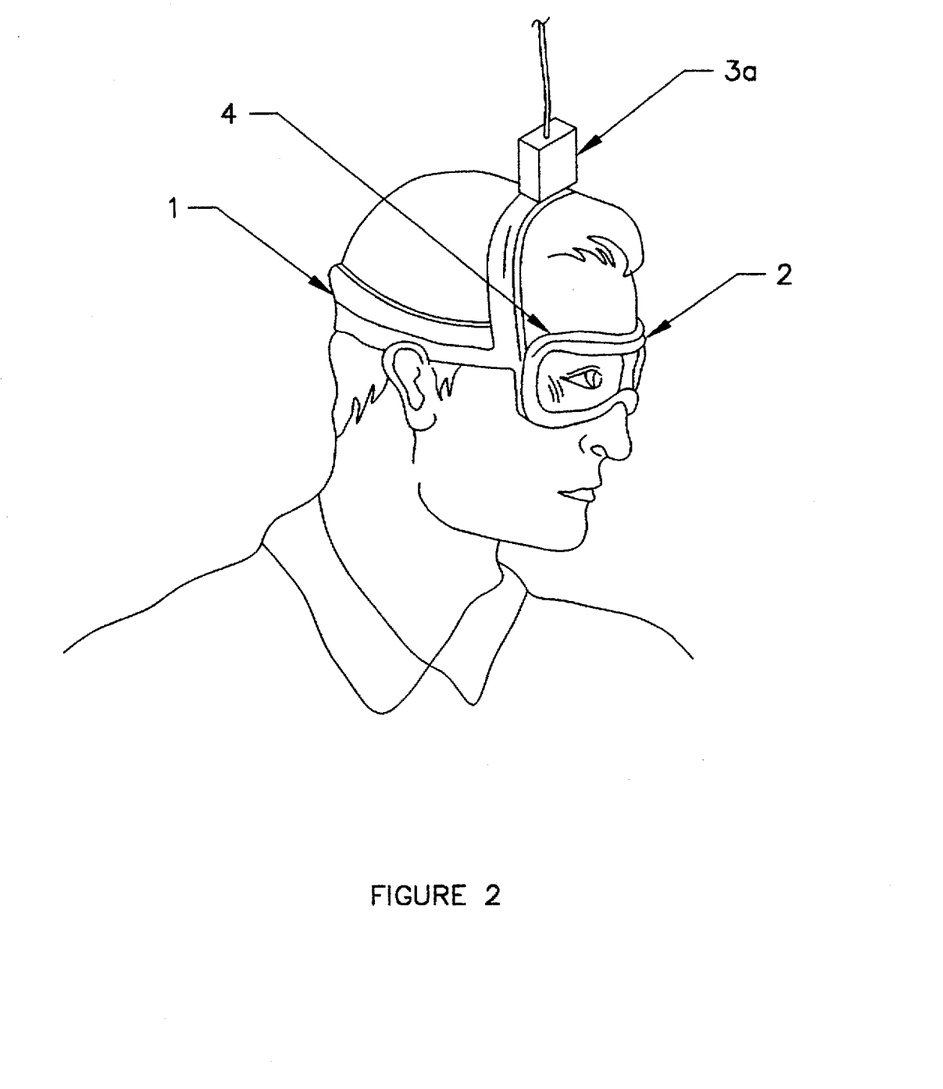
FIG. 2 depicts the goggles, the electrooculographic (EOG) sensor system and the head position and orientation sensor all mounted on a headset.
Figure 3:
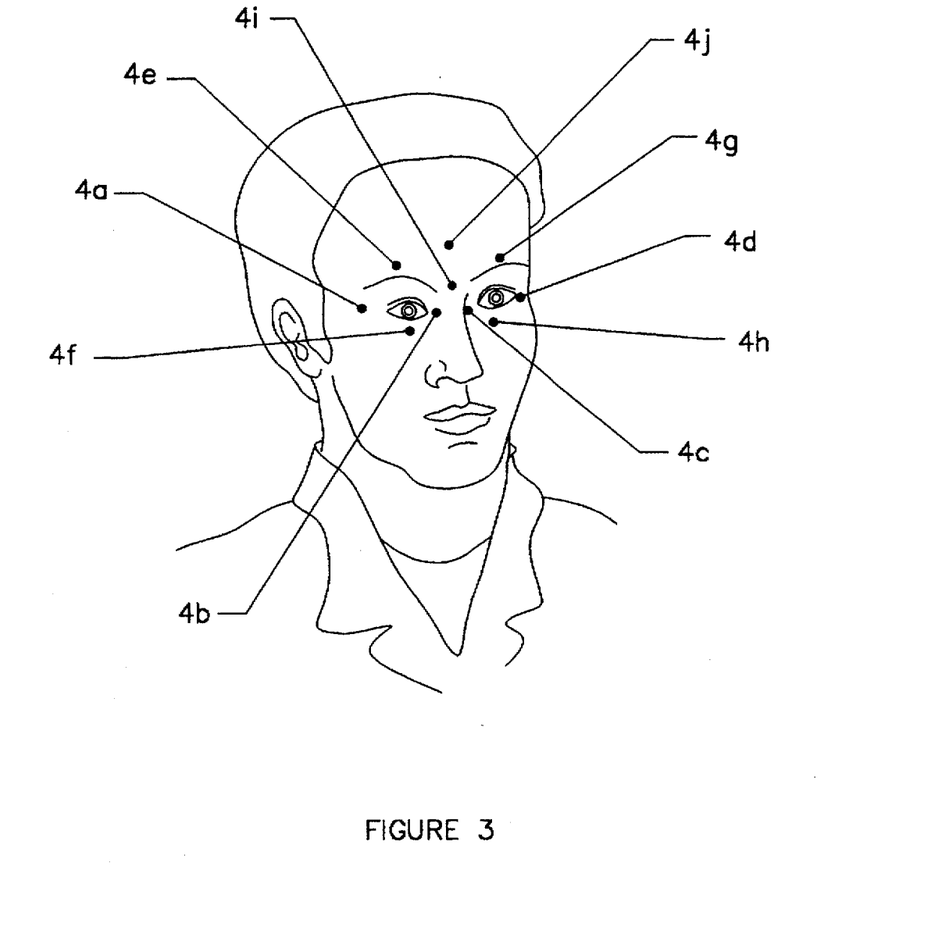
FIG. 3 depicts a skin surface electrode configuration for the goggle embedded electrooculographic (EOG) sensor system.

FIG. 2 depicts the user with the headset 1 holding the goggles 2 and supporting the head position and orientation sensor 3a. The skin-surface electrode sensors 4, used for the measurement of the left and right eye vertical and horizontal electrooculogramic signals, are embedded in the holder for the goggles 2 which fits around the eyes. The electrode configuration as shown in FIG. 3 consists of a periocular electrode array for each eye, with two electrodes located horizontally at opposing temporal canthi sites $4a$ and $4d$, two electrodes mounted on the nasal canthi sites $4b$ and $4c$, and two more electrodes located vertically for each eye at opposing sites one above the eyebrow and the other below the eye at the infraobital foramen ($4f$ and $4h$ for the left eye and $4e$ and $4g$ for the right). The electrodes are in an unipolar recording configuration with an indifference reference electrode located at the frontal sinus site $4i$ on the forehead and an amplifier ground at $4j$.

The skin surface electrodes are made from conductive cloth sensors embedded in the neoprene holder for the goggles 2. The conductive cloth sensors are made from woven, stretchable, nylon fabric impregnated with silver particles. The ohmic resistance for this material is very low and stable; lead wire bonding is achieved by use of a conductive epoxy. The fabric sensor conforms easily to body contours, and the lightness and flexibility of the sensor allows the user to wear the electrodes for long periods without discomfort. A porous fabric supporting an electroconductive gel is placed between the skin and electrode sensor material. The fabric is shaped as an insert to the inner surface of the neoprene holder for the goggles 2 and it is gelled only at the electrode contact points. The user applies a skin preparation to the skin surface to remove skin oil and outer dead skin cells before fitting the headset 1, to reduce skin resistance to an acceptable level.

Figure 4:
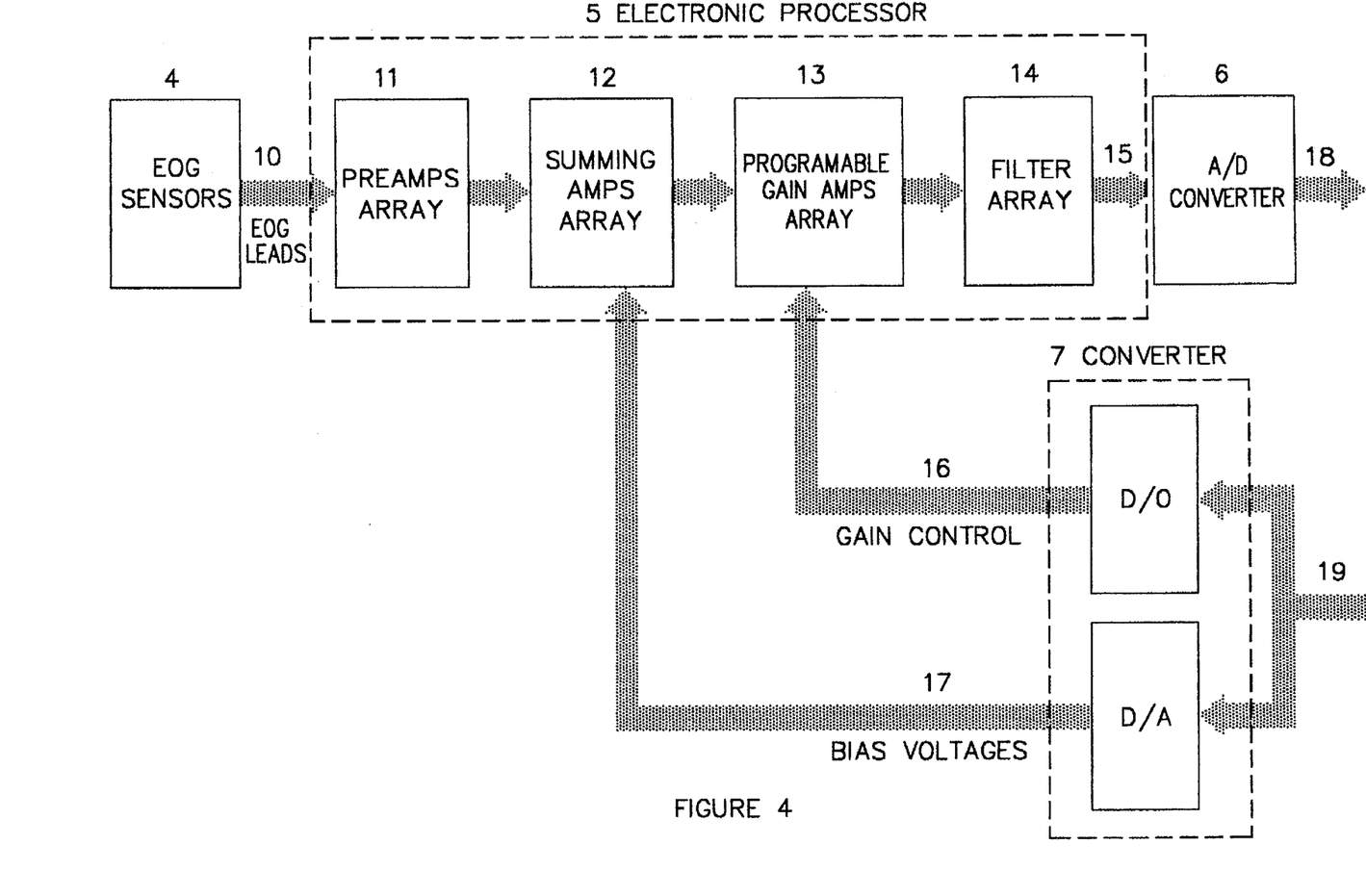
FIG. 4 depicts a block diagram for the electronic components of the electronic processor.

FIG. 4 depicts a block diagram of the electronic processor 5 components of the invention. The analog EOG signals 10 from the electrodes 4 are amplified by an array of preamplifiers 11. The preamplifiers are two-channel, input buffered, differential-input instrumentation amplifiers with high input impedance, high gain, high common-mode rejection ratio (CMRR), low noise, and appropriate isolation to safeguard the user from electrical shock. The array supports an unipolar recording configuration with a separate amplifier for each of the electrode leads $4a$–$4g$. The electrode $4i$ is used as a common reference for the second channel of each amplifier in the configuration and the forehead electrode $4j$ is used as amplifier ground. The electrode leads to the preamplifiers are twisted and the amplifiers and components are housed in a shielded enclosure to reduce interference from outside sources of electromagnetic energy.

An array of bias adjustment amplifiers 12 is used to reduce the contributions from the direct current (DC) offset potential induced at the interface between the electrodes and the skin surface. This potential is on the order of 5–10 millivolts and is commonly much greater in magnitude than the signal component. The outputs of the bias adjustment array are further amplified by an array of second stage programmable gain amplifiers 13. The amplifier stages are battery powered and the outputs are transmitted through optocouplers to provide electrical isolation for user's safety.

The offset voltages for the bias adjustment amplifiers and the programmable gains are continually updated by the digital computer 8 and reset via the converter 7. This feature is essential in practice as the DC potentials generated by the electrode-skin interface, and the retinal potentials tend over time to drift out of the dynamic range of the amplifiers resulting in overrange and saturated amplifiers with clamped output voltages. The DC bias offset voltages in conjunction with the programmable gains are used to maintain the resulting output voltages within the proper ranges determined by the power supply.

After the second stage amplification, the signals are filtered to remove externally induced noise. The analog electrical outputs from the amplifiers are the inputs to an array of active element lowpass filters 14 used for noise cancellation in EOG measurements. A notch filter may be used to remove power line artifacts. However, satisfactory noise filtering is accompanied by an undesirable distortion in the underlying step signal. This can result in an overestimation of the saccade duration and an underestimation of the peak velocity.

Figure 4A:
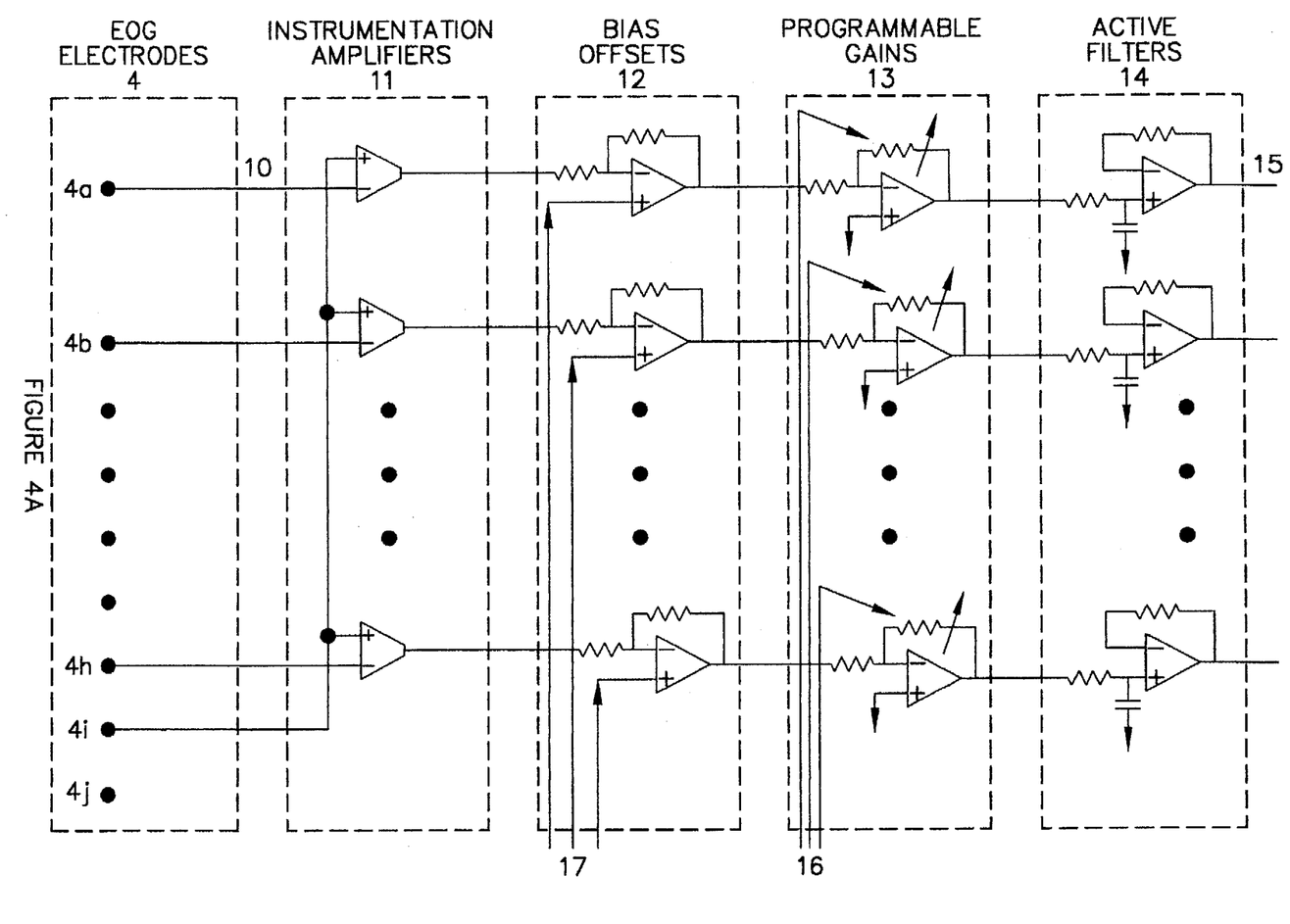
FIG. 4a depicts a schematic of the components for the electronic processor.

As sketched in FIG. 4a, a schematic of the components for the electronic processor, the amplifier and filtering arrays are arranged in a cascading series, with the output of a preamplifier 11 for a single electrode 4, connected to the input to a bias adjustment amplifier 12, which is in turn connected to an amplifier 13 and finally to an analog filter 14. The filtered outputs are the analog electrical inputs 15 to the multiplexing analog-to-digital converter 6 with a digital electrical output connected to the input 18 of the digital computer 8. The schematic shows the functional relation between the circuit elements; the actual circuit design can differ.

Figure 5:
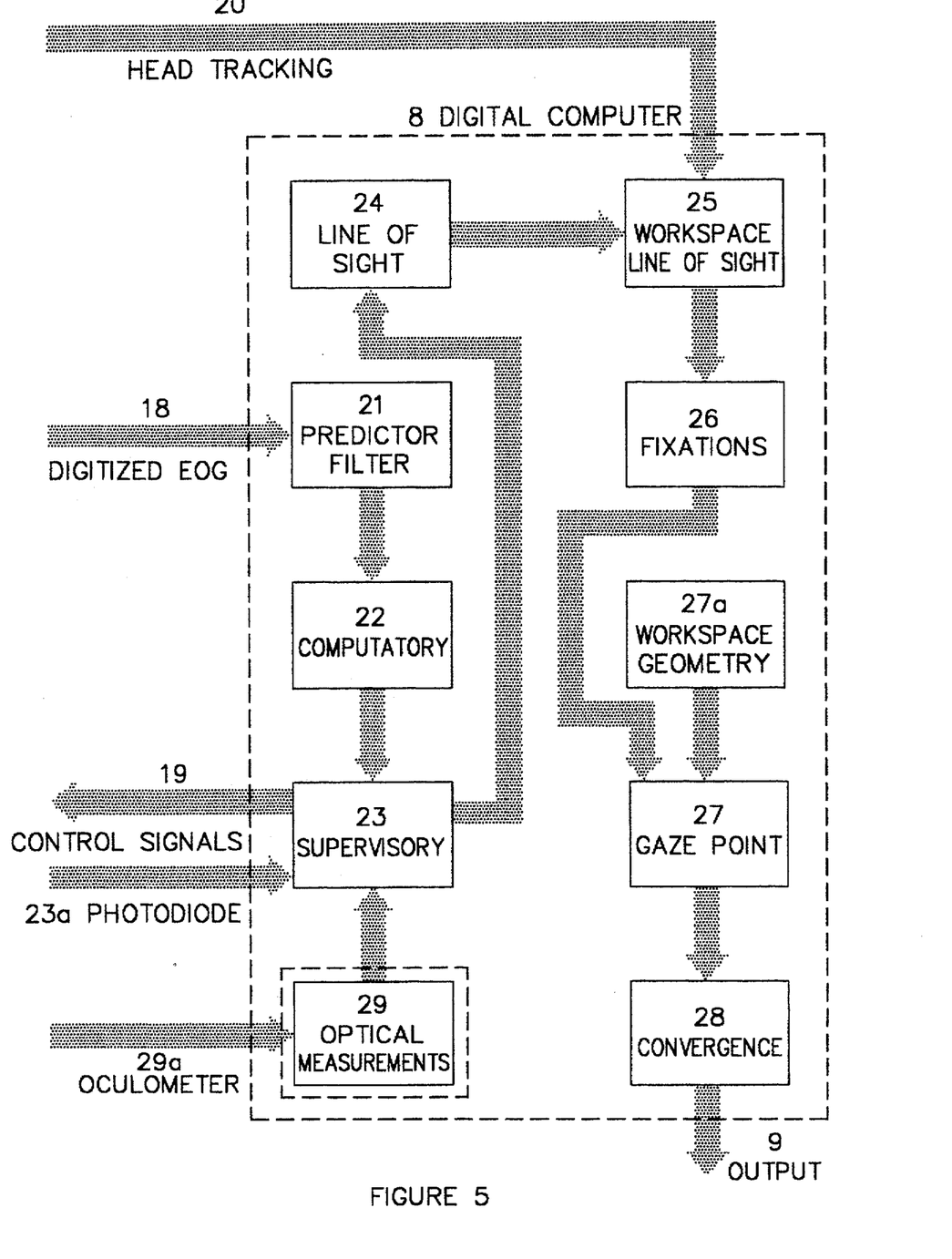
FIG. 5 depicts a block diagram for the computer programs of the digital computer.

FIG. 5 is a block diagram showing the relations among the computer programs of the digital computer 8. The digital electrical input 18 is processed by computer routine 21 acting as a digital estimation filter for the EOG signals. The estimated signals are input to a computatory routine 22 which uses the signal values to solve for the ocular angular offsets, the retinal potential and muscular artifacts from the sum and difference signals for the horizontal and vertical EOGs. These values are input to a supervisory routine 23 which uses the retinal potential estimations to compute gain and offset bias voltages for the amplifiers 12 and 13.

The estimator filter 21 estimate the true EOG signals from the digital signals 18 correcting for the measurement noise in the process. The filter uses the corresponding present digital output values (present measurements), past estimated values and an estimate of the measurement process noise power in the computation of the true signal estimates; the filter for each measurement channel, combines the previous estimate with the current measurement to account for the relative accuracies of the two quantities. In a further embodiment, the estimator filter 21 is a recursive predictor-corrector Kalman filter. The filter coefficients are determined in calibration prior to application.

The computatory routine 22 forms the sum and difference voltage potentials for the horizontal and vertical EOGs for each eye from the individual electrode signals estimated by routine 21. The routine uses the sum and difference potentials for the horizontal and vertical EOGs to solve for the ocular angular offsets, the retinal potential and muscular artifacts. The approach used is based on an unique relationship between the sum and difference of the EOG potentials from opposing electrodes. The relation is mathematically derived from a three dimensional model of the electrostatic field for the retinal dipole as a function of the ocular orientation. From this relation, it can be shown for the retinal dipole that the potential difference between opposing electrodes is mathematically determined by the product of: (1) the retinal potential (defining the dipole moment), (2) a geometrical factor, and (3) the trigonometric sine of the angle of ocular rotation in the direction defined by a circular arc connecting the electrodes. Similarly, the sum of the potentials of the opposing electrodes is determined by the product of: (1) the retinal potential, (2) a geometrical factor, and (3) the cosine of the rotational angle. The potential ground is assumed to be referenced to the angular boresight direction located midway between the electrodes. The geometric factors are a function of the electrode configuration as fixed by the holder for the goggles 2; the factors are derived from equations for the resulting dipole electrostatic field.

For example, the estimated signals for electrodes 4a and 4b are a horizontal pairing for the right eye, with the reference ground for the pairing being the average of the sum of the voltages for the electrodes 4e and 4f. The potential for either electrode is the electrode signal minus that for the reference ground. The sum of the potentials for electrodes 4a and 4b are the sum potential for the horizontal EOG of the right eye, while the difference is the difference potential. Similarly, the estimated signals for electrodes 4e and 4f are a vertical pairing for the right eye; the reference ground is the average of the sum of the voltages for the electrodes 4a and 4b. Again, the potential for either electrode is the electrode signal minus that for the reference ground. The sum of the potentials for electrodes 4e and 4f are the sum potential for the vertical EOG of the right eye, while the difference is the difference potential.

The equations for the difference (dVh) and sum (sVh) potentials for the horizontal electrodes, are:

$$dVh = p*Adh*\sin(ah) + Bdh*vm + DCdh, \text{ and}$$

$$sVh = p*Ash*\cos(ah) + Bsh*vm + DCsh,$$

where p is the retinal dipole moment, ah is the ocular offset in the direction connecting the horizontal electrodes, and Adh and Ash are constants of proportionality defined by the reference viewing direction and the goggle 2 configuration as derived from equations for the dipole electrostatic field, and are determined in the calibration process. Here, vm is the muscular artifact and Bdh and Bsh are constants. The contributions from the electrode direct current bias voltages are denoted by DCdh and DCsh.

Similarly, the equations for the difference (dVv) and sum (sVv) potentials for the vertical electrodes, are:

$$dVv = p*Adv*\sin(av) + Bdv*vm + DCdv, \text{ and}$$

$$sVv = p*Asv*\cos(av) + Bsv*vm + DCsv,$$

where, as above, p is the retinal dipole moment, av is the ocular offset in the direction connecting the vertical electrodes, and Adv and Asv are constants of proportionality defined by the reference viewing direction and the goggle 2 configuration as derived from equations for the dipole electrostatic field, and are determined in a calibration process. Again, vm is the muscular artifact and Bdv and Bsv are constants. The contributions from the electrode direct current bias voltages are denoted by DCdv and DCsv.

The set of equations may be solved using the Broyden Algorithm, a variation of the Newton's iterative method of numerical analysis for solving nonlinear systems of equations. The iteration process will converge to a solution vector containing the unknown retinal dipole moment, the angular offsets and the muscular artifact, provided that an accurate starting vector is known and the inverse of the corresponding Jacobian matrix exists at that solution. However, the effect of the muscular artifact on the relations for the horizontal potentials is trivial (i.e., Bdh and Bsh are close to zero in value) and the set of reduced equations may be solved directly; a sensible starting vector for the Newton's iterative method is the direct solution to the reduced set of equations.

The contributions from the electrode direct current bias voltages to the above equations, for the sum and difference potentials, are stable over long term and determined in an initial calibration process. However, as a check on the electrode bias voltages, routine 22 computes an update during fixation periods in eye movements. As described below in further detail, routine 26 determines fixation periods in the user's eye movements; these are periods where the user fixates on a visual cue without ocular movement. The eye movement state is flagged in global common by routine 26; the ocular offsets are unchanging and muscular artifacts are uncommon during these periods. For these reasons, during these periods routine 22 computes the rate of drift in electrode direct current bias voltages from the time derivatives of the sum and difference potentials and the dipole moment. The routine keeps running records of the smoothed time history of the sum and difference potentials, the dipole moment and the muscular artifacts. The time derivatives of the above equations gives the following expressions for the rate of change of the sum and differences of the electrode bias voltages during fixations when muscular artifacts are not present, $$DCd = dV - p*Ad*\sin(a), \text{ and}$$

$$DCs = sV - p*As*\cos(a),$$

where the superscript dot indicates time derivative and the equations apply to both horizontal and vertical opposing electrodes. These time derivatives are used to compute updated values of the sum and difference electrode bias voltages by using numerical analysis integration techniques. The bias voltages of the opposing electrodes are then computed from the corresponding sum and differences; these electrode direct current bias voltages are stored in global common.

The supervisory routine 23 computes DC bias offset voltages and gains for the amplifier arrays 12 and 13, respectively. Routine 23 provides a continual update of the bias voltages and amplifier gains to ensure that the output voltages are within the limits of the power supplies and therefore that the amplifiers will not be clamped. The change in retinal dipole moment with light adaptation and the gradual drift in electrode bias voltages causes changes in the measured EOG voltages. The routine 23 has access to the running record provided by routine 22 of smoothed values for the retinal dipole moment, the ocular angular offsets, the muscular artifact and the electrode bias voltages, and predicts the changing values from the past history. The routine computes the amplifier gains and bias offset voltages needed to maximize amplifier sensitivity while maintaining stability. The routine provides an electrical digital output 19 to the digital-to-analog converter and digital-output device 7 which in turn provides the digital electrical input 16 for the programmed gains of the amplifier array 13, and the analog electrical input 17 for the bias offset voltages of the bias adjustment amplifier array 12. The amplifier bias offset voltage levels and gains are stored in global common for the computations of routine 22.

In a further embodiment, routine 23 reads the output of a photodiode to estimate the ambient light level facing the user. The photodiode is mounted on the goggles 2 within the visual field of view of the user and measures the ambient light level seen by him; an amplifier converts the photosensitive reverse current of the diode into a voltage level, and the resulting amplified analog electrical output is digitized by an A/D converter, the digital output of which is input 23a to routine 23. While the electrode bias voltage is not effected by light level, the value of the retinal dipole moment changes with light adaptation which is a function of the change in pupil diameter with the lighting level being viewed. The response is light spectrum dependent; in red colored light which causes minimal changes, the steady state retinal dipole moment for light adaptation is roughly twice that for dark adaptation. In this embodiment, routine 23 employs expert knowledge taken from the literature about the time response of pupil diameter to lighting levels and the resulting dark and light adaptation levels, to predict the future change in retinal dipole moment from the time history of the ambient lighting and that of the dipole moment. This prediction is used to compute the needed values of amplifier gains and bias offset voltages. The ambient light level for the visual field is only a rough measure of the illuminance from the visual element momentarily being viewed and for this reason, the predicted change is only approximate; however, the additional knowledge of the lighting environment provided by the photodiode return improves the predictability over that of the dipole moment history alone, and therefore improves the supervisory control by routine 23.

In a still further embodiment, the invention can be used as a component of an oculometric system, to supplement the operation of an optical oculometer; while the optical technology is used to image the eye within a limited central field of view, the invention is used to track viewing outside the central field. This design expands the effective tracking field of view beyond that of the optical technologies, to cover wider and more natural visual search fields. In this design, the supervisory routine 23 receives input from a routine 29 which determines the ocular offsets from digital electrical input 29a from an optical oculometer. The routine 23 compares the ocular offsets from the two technologies and if the offset is within the central tracking field, accepts the optical measurement. The occurrence of several viewings within the central field allows automated intermittent calibration and adjustment of the amplifier bias voltages to further account for the long term skin surface electrode direct current drift. The successive occurrence of two viewings within the central tracking field enables the direct computation of the long term electrode direct current bias voltage drift for each of the electrodes. These values are stored in global common along with the amplifiers bias voltages and gains for the computations of routine 22, and the central viewing flag status. In this further embodiment, the computations of the electrode bias voltages are not performed by routine 22 during fixations within the central viewing field; the values default to the routine 23 computations.

The ocular angular offsets from routine 22 (or as selected by routine 23 in a further embodiment for an expanded oculometric system), are used by a series of computer 8 routines to compute visual lines of sight, classify the sights as fixations or saccades, and group the fixations into gaze points for output 9. FIG. 5 shows that the ocular angular offsets from routine 22 (routine 23) are inputs to routine 24; this routine computes the optical axis from the angular offsets and the resulting viewing direction relative to the optical axis. In turn, the routine 25 reads the digital electrical input 20 for the head position and orientation from the head tracker 3 and transforms the visual line of sight into the workspace line of sight for the real or virtual workspace which the user is viewing through the goggles 2. The routine 26 maintains a running record of the workspace lines of sight and classifies the eye patterns as fixations, saccadic movements, or pursuit tracking. Finally, the routine 27 groups the eye fixations into cognitive meaningful gaze points and movements. The gaze points for both eyes are used by routine 28 to compute a binocular convergence point for a dual eye system; the result from routine 27 (or routine 28 for a dual eye system) is the digital computer output 9.

The routine 24 computes the visual line of sight from the optical axis defined by the ocular angular offsets. The ocular angular offsets determine the angular orientation of the ocular optical axis which is naturally aligned with the electrostatic dipole of the eye. Routine 24 first computes directional cosines for the optical axis in the headset coordinates from these values. The optical axis is assumed to rotate about the ideal rotational point of the eye in the optical orbit of the skull. The center of rotation of the eye is located approximately 13 millimeters behind the front surface of the cornea. The result is an accurate description of the optical axis and rotational center in the headset coordinate system.

However, the optical axis of the eye does not coincide with the visual axis (the line connecting the fovea to the point of fixation) by 5 to 7 degrees. The visual axis extends from the first Gaussian nodal point of the eye (normally near the center of curvature of the corneal anterior surface) and is commonly perpendicular to the cornea; it is generally directed 5 degrees inwards to the optical axis and 2 to 3 degrees upward. The visual axis is defined by an origin point in the optical axes coordinate system and three directional cosines, which are determined in an initial calibration process. These parameters defining the visual axis, are transformed into coordinates for the headset coordinate system by routine 24 from the relations for the optical axis. The result is an accurate specification of the visual axis.

The headset is rigidly made and the headset coordinate system is defined by the construction of the headset and the placement of the goggles and head sensor on the headset. The headset is assumed fixed on the head; for this reason, the optical orbit is fixed relative to the headset and consequently, the rotational point of the eye is assumed stationary in the head coordinate system and is determined in calibration. Similarly, the eye is assumed not to roll in the optical orbit due to operational limitations in head orientation tilts; therefore the spatial relation of the visual axis relative to the optical axis is fixed in the headset coordinate system and is determined in calibration.

The computer routine 25 computes the user's viewing origin and direction in the visual workspace from the viewing point and axis given in the headset 1 coordinates. In some applications, the user may be viewing through the goggles 2, an external real or virtual workspace which is independent of the headset; the goggles may be open or part of a head-mounted virtual reality display. In this case, the visual line of sight computed by routine 24, is transformed to that for the external workspace following location of the headset in the workspace; the position coordinates and directional cosines of the orientation of the tracking system source 3b in the workspace are listed in a computer memory data file.

The tracking system 3 used to measure the position and orientation of the headset 1, consists of a sensor 3a, source 3b, and electronics processor 3c. The source is mounted in the user's workspace; the sensor is mounted on the headset 1. The system allows continual tracking of the six degrees of spatial freedom; the processing unit continually computes the position and orientation of the sensor relative to the source, and controls the transmission of the output data. Tracking systems are available employing different sources: infrared, ultrasonic, optical, and magnetic fields. The output of the processor 3c is the digital electrical input 20 to the digital computer 8; the input is read by routine 25.

The computer routine 26 isolates fixations from the line-of-sight data by performing as an expert system, classifying the immediate visual state defined by the workspace viewing direction, as fixation, saccade, pursuit or blink from an embedded expert knowledge base of these ocular states. The computer expert system functions from a preprogrammed understanding of the visual process. For example, when studying a static visual display, the eye is continually rotating and fixating different portions of the scene; for this reason, the eye gaze consists of sudden saccadic jumps with interposed slightly jittery fixations. These movements are made possible by three sets of extraocular muscles which control the movement and positioning of the eye. These muscle pairs include the horizontal and vertical rectus muscles, the lateral and medial rectus muscles, and the inferior and superior oblique muscles. Each pair of muscles exerts effort in a different axis, so that the eye is capable of movement to an extremely large number of positions. Some of the movements are involuntary and involve compensatory responses to movements of the head or to stimulation of certain facial nerves.

The saccadic jumps which move the eye between fixations are sudden and rapid ballistic movements lasting about 30 to 120 milliseconds and traversing 15 to 40 degrees. The peak velocity for a 10 degree saccade can reach 450 degrees per second; the peak velocity for a 20 degree saccade can range from 290 to 400 degrees per second. Vision is suppressed during a saccade. A 200 millisecond refractory period is required for recovery before another saccade can be executed.

The fixation following a saccade is a brief period of relative stability which allows that portion of the scene within the foveal vision to be studied. The fixation period is typically from 200 to 600 milliseconds. Small jittery motions occur during a fixation; these motions are composed of slight drifts with amplitudes less than one degree, followed by microsaccadic corrections. A low amplitude, high frequency tremor is superimposed. The purpose of a saccade is to rotate the eye so that the image of a cue in the visual scene falls within the foveal vision. The image is then studied during the fixation; the microsaccadic movements induce changes in the image required for seeing. However, the eye seldom remains in one fixation for long.

On the other hand, pursuit movements are slow involuntary eye tracking movements which smoothly follow a moving object of interest in the visual field. Pursuit movements have an initial reaction time of 0.12 to 0.25 seconds and are limited to a maximum velocity of 25 to 30 degrees per second. While the saccadic control system acts as position servomechanism directing the fovea of the eye to a target, the pursuit system acts as a velocity servomechanism rotating the eye at the same angular rate as a target.

Finally, blinks start slightly before or simultaneously with upward directed saccades, but never after the eye movement. In contrast, blinks are sometimes initiated after the onset of downward directed saccades. It has been reported that only in less than one percent of blinks is there apparent eye movement. Blinks usually last from 20 to 200 milliseconds with the longest observed terminating smoothly around 300 milliseconds.

The routine 26 detects saccades and predicts fixation end points, as well as separates saccades from pursuit eye tracking of moving targets, and eye blinks. The routine uses an automatic fixation and saccade classification scheme operated in conjunction with a saccadic end point predictor. The classification scheme is a combination of these two methods: the position variance method 26a and the velocity detection method 26b, operated as parallel processing channels. The end point predictor 26c is derived from a knowledge base on the relation between saccade peak velocity and amplitude of movement. The position variance method 26a is based on the expert knowledge that a fixation is characterized by relative immobility with low variance in eye movement, while a saccade is distinguished by rapid change (high variance) in position. In this method, the means and variances are computed for a sliding window of time samples in eye position. The variance of the windowed samples for a fixation is lower than an empirically determined threshold level. When a saccade occurs the variance rises, reaches a peak and then subsides toward the fixation level again. The initiation and termination of a saccade is automatically detected by comparing the position variance to the threshold level determined in an initial calibration process. Furthermore, curve fitting to the variance function is used to make predictions about the future variance values and therefore the time and location of the next fixation. The method has a time lag attributable to the width of the sampling window.

The velocity detection method 26b operates in parallel. In this method, the eye movement speed is computed from the windowed samples by first smoothing with a low-pass digital filter to remove noise, and then numerically differentiated. The computed speed is compared to an empirically determined threshold level separating saccadic movements from fixations. A speed above the threshold is classified as saccadic while that less than the threshold is classified as fixation. The position variance and velocity methods give similar results. These two methods are combined to obtain a more reliable saccade discriminator. The combined method can be based on either the agreement between the separate threshold outputs, or more elaborately, upon saccade state-probability estimates derived from the magnitudes of the position variance and speed measurements.

The saccadic end point predictor 26c is activated once a saccade has been detected. This method predicting the end point of the saccadic movement from the peak velocity, discriminates between saccades and pursuit tracking. The predictor is based on the expert knowledge that the eye-movement velocity function during a saccade is nearly symmetrical about a peak velocity located approximately half-way to the next fixation. In detail, the saccadic velocity function rises above the threshold detection level, accelerates to a peak velocity about half-way to the next fixation, and then decelerates below the threshold at the fixation point. Although it has been reported in the literature that a sine wave is a good fit for the velocity function, the function is in fact, more or less symmetrical depending upon the magnitude of the peak velocity. In actuality, the saccadal amplitude is related to the maximum velocity by an exponential function using curve fitting constants. A look up table contains empirically determined correction factors needed to adjust for the asymmetry in the velocity function. The correction factors are derived in the calibration process. Therefore, the processor by detecting the peak of the saccadal velocity, uses the relation to the saccadal amplitude to predict the termination time and location of the next fixation. A classification as saccadal movement that does not satisfy the end point predictor is reclassified as pursuit movement; these movements are less than 30 degrees per second. The eye movement status is stored in global common for reference by routine 22.

The computer routine 27 groups the fixation data into task related visual gazes. The user tends to view a task related visual element with a sequence of fixations all in the same display area connected by small saccades. These fixations grouped together form a single gaze that more closely approximates the user's cognitive functioning. The routine 27 uses a retrospective algorithm to determine the start, continuation, and termination of each gaze point as follows:

(1) A 100 millisecond sequence of eye fixations within 0.5 degrees of each other defines the start of a gaze point; the gaze point center is the mean of the eye fixations. The algorithm delay of 100 milliseconds is undetectable to the user.

(2) The gaze point is continued as long as eye fixations remain within one degree of the current gaze point center. The gaze dwell time is the sum of the 100 millisecond start time and the current continuation time.

(3) A 50 millisecond sequence of eye positions that are beyond one degree of the current gaze point defines the termination of the present gaze. A blink up to 200 milliseconds is allowed without termination.

The routine 27 computes the gaze point as the visual viewing point of the eye as computed by routine 26 for pursuit tracking; initially pursuit tracking will consist of a saccade to acquire the target on the fovea followed by steady tracking. A rate varying target will be tracked with saccadic updating in tracking rate.

The viewed point in the user's visual workspace is then computed using computer graphics concepts and a computer memory data base listing the objects and their locations in the user's workspace. The routine 27 computes the point of intersection of the viewing direction with each workspace surface facing the user from the surface normal and the location of a vertex. The routine checks to ensure that the intersection point is within the edges containing the surface. The viewed point is the contained intersection point closest to the user's eye.

The positions and orientations of the surfaces of the objects in the user's visual workspace are listed in a digital memory computer data file 27a by the directional cosines of the normals to the surfaces and the coordinates of the vertices. The surfaces of the objects are described by a piece-wise net of planar segments for computational purposes. Note that the objects being viewed for a virtual workspace are those generated by the drawing file for the display driver of video display; in this case, the digital memory computer data file 27a is defined by the virtual workspace used to set up the display driver.

The routine 28 computes the convergence points of the left and right eye gaze directions for a dual eyetracker configuration. The convergence points are the points of closest approach between the two gaze lines when non-intersecting; the line segment connecting the two lines at these points are perpendicular to both lines.

The accuracy of these computations is dependent upon an initial calibration process in which the user gazes in turn at a series of cue markers displayed at predetermined locations on a visual display. The display is of uniform brightness with a predominately red hue, at the same level as the ambient surround, and the cue markers are color contrasted with the display, to ensure constant retinal dipole moments. Following the user's light adaptation and the initial fitting of the amplifiers' gain and bias offset voltages, sightings on 13 different cue markers allows the computation of the constants of the EOG equations listed above for routine 22. Next, the data collected for the locations of the cue markers and the resulting viewing angles, is used to solve for characteristics of the user's eye. The relation of the viewing axis to the optical axis is determined by solving for the axis origin and the directional cosines in the optical axis coordinate system. The center of ocular rotation and the alignment of the optical axis coordinate system is located in the coordinate system of the headset 1. The invention is auto-calibrating with a color contrast video display of uniform brightness since the user can quickly and accurately go through the calibration procedure.

The calibration can be intermittently automated when the invention is used as a component of an expanded oculometric system, to supplement the operation of an oculometer based on optical technology; the invention is used to track viewing outside the central field of view within which the optical technology is used to image the eye. This design allows automated calibration of the invention when the user is viewing within the central field of view shared by both components. The occurrence of six viewings within the central tracking field allows the initial computation of the constants of the EOG equations and the characteristics of the user's eye, with the viewing offsets having been determined by the oculometer. Further viewings allows the continual calibration of these parameters. As mentioned above for routine 23, the successive occurrence of two viewings within the central tracking field enables the updating of the long term electrode direct current bias voltage drift for each of the electrodes.

Figure 6:
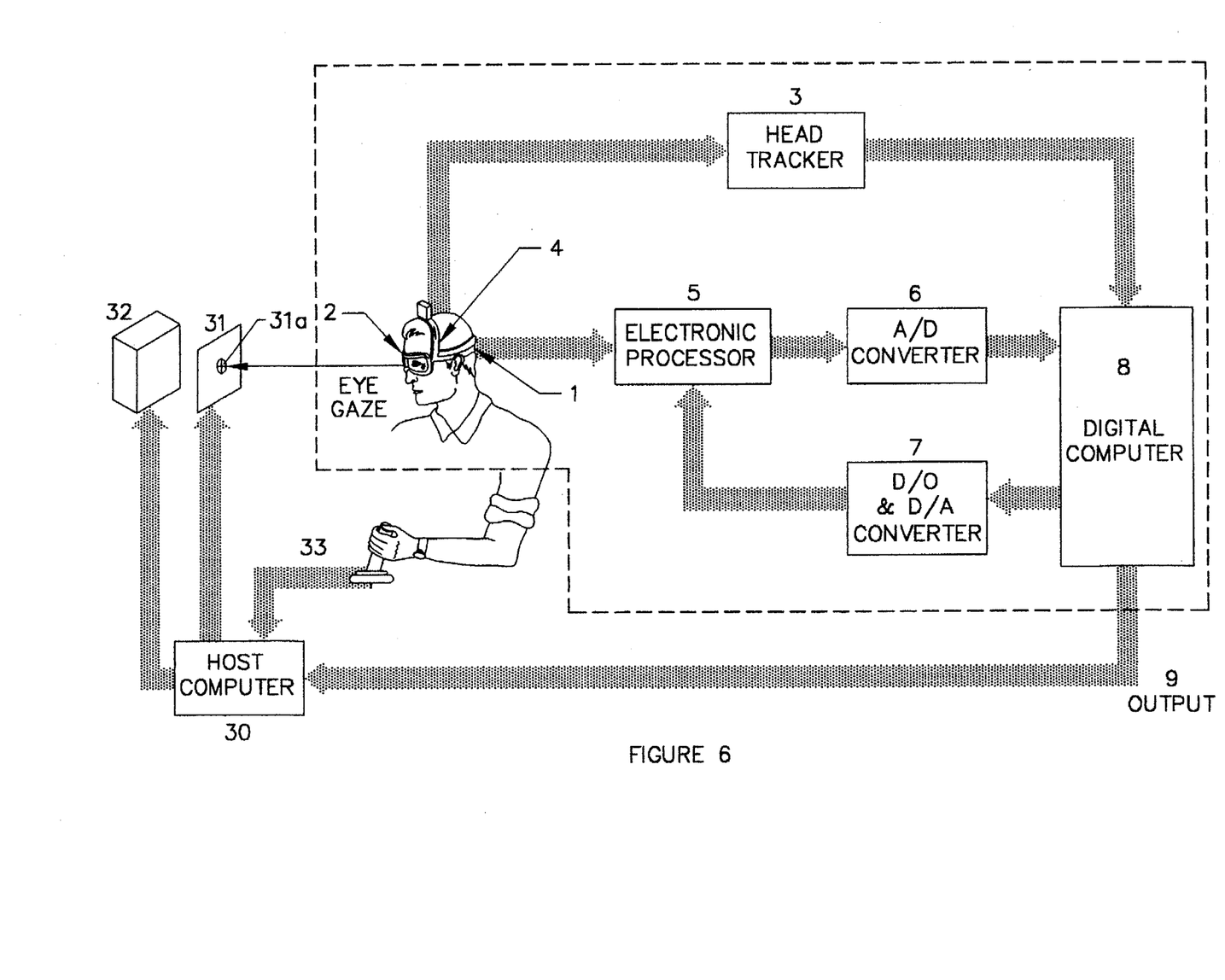
FIG. 6 depicts a block diagram for the application of the invention to the control of computerized machinery.

The invention by design can serve as a peripheral to a host computer system 30. The outputs 9 of the digital computer 8 are updates on the eye gaze status, fixation location (in the workspace), and dwell time. The output 9 can be inputted to a computer driving a display 31 for operator control of a machine process 32. The operator using the invention, interacts with the display by ocular functions in real time. The gaze fixation point of regard indicates a point of visual attention on the display. The subject will look over the display to acquire information as well as to initiate changes to the process and therefore the display. The interest component of the continuation flag, set for a long fixation dwell time, may be used to indicate selection of a display icon. A comparison of the fixation location with the positions of the display icons 31a will determine which icon is of interest. The corresponding icon may be highlighted by the computer for feedback to the operator. A motor action 33 by the operator, such as a button push or voice command to an automatic speech recognizer, may be used to confirm a selection. Of course, the process change with the accompanying display update is determined by the display driver program and the icon selected.

The accuracy of an oculometer may be limited by the angular size of the human foveal vision (+/−0.5 degrees); the visual scene is integrated in the visual cortex as ocular fixations occur about the scene. However, the operator of a computer driven tactical display may wish to select between icons that are closer than this size and perhaps even overlap. For this reason, a companion display to the tactical display may be shown by toggle switch action, either adjacent or as overlap showing the icons by order of designation separated at 0.5 degree increments. The operator then looks at the companion display to make the selection.

The invention has applications to the real-time determination of visual workload. The EOG is a continuous analog signal and it can be sampled at a rate high enough for the accurate determination of the duration of the eye blink and the onset of a visual fixation. The duration of the endogenous eye blink is a measure of the visual attention that is being dedicated to a task by the human viewer. While short closure durations and low blink rates are associated with visual attention, increased blink rates and longer blink durations occur with the buildup of operator fatigue. The differences in the blink durations for these conditions are commonly on the order of milliseconds. Similarly, because of the high sampling rate, the invention measures the start of visual fixation with sufficient accuracy to align the event with the measurements of the cerebral potential. This feature is of interest for applications that utilize the relations between brain waves and eye movements.

Obviously, many modifications and variations of the present invention are possible in light of the above teachings. It is therefore to be understood that, within the scope of the appended claims, the invention may be practiced otherwise than as specifically described.

I claim:

1. A method for determining ocular gaze point of regard and fixation duration of a person, comprising the steps of:

sensing the electrooculographic potentials of the eye with a periocularly placed unipolar skin-surface electrode configuration having a common reference;

amplifying, digitizing and adaptively filtering said electrooculographic potentials;

computing head related ocular angular offset in the direction connecting opposing periocularly placed electrodes, along with the corresponding retinal dipole moment, muscular artifact and electrode direct current bias voltage, from said electrooculographic potentials for said opposing periocularly placed electrodes;

computing gains and DC bias offset voltages from a running history of said retinal dippole moments, muscular artifacts and electrode direct current bias voltages, for amplifiers of said electrooculographic potentials;

applying said amplifier gains and DC bias offset voltages to said amplifiers of said electrooculographic potentials to maximize signal sensitivity while precluding saturation of the amplified signals;

determining the position and orientation of the person's head;

computing viewing direction with respect to the workspace from said ocular angular directions and said position and orientation of the person's head;

determining ocular fixations by utilizing automatic fixation and saccade classifications schemes and a velocity based prediction scheme; and grouping said fixations into gaze points of regard.

2. The method of claim 1 wherein said step of computing head related ocular angular offset in the direction connecting said opposing periocularly placed electrodes is computed along with the corresponding retinal dipole moment, muscular artifact and electrode direct current bias voltage by the steps of:

computing voltage potentials for opposing periocularly placed electrodes from the measured electrode potentials and the potential ground referenced to an angular boresight direction located midway between the electrodes;

computing sums and differences from the voltage potentials of the opposing periocularly placed electrodes;

computing said angular offset (az) and the corresponding retinal dipole moment and muscular artifacts, from the following equations, for the corresponding difference (dC) and sum (sV) potentials:

$$dV = p*Ad*\sin(az)+Bd*vm+Dcd,$$

$$sV = p*As*\cos(az)+Bs*vm+Dcs,$$

where p is the retinal dipole moment, Ad and As are constants of proportionality defined by the reference viewing direction and the electrode configuration, vm is the muscular artifact due to blinks, eyelid lag and facial muscle movements, Bd and Bs are constants of proportionality, and the contributions from the electrode direct current bias voltages which stablize over long term and are determined in an initial calibration process are denoted by Dcd and Dcs; and updating the electrode direct current bias voltages during fixation periods in eye movements, when the ocular offsets are unchanging, from the rate of drift in electrode direct current bias voltages computed from the time derivatives of the sum and difference potentials and the dipole moment, said time derivatives being used to compute updated values of the sum and difference electrode bias voltages and the bias voltages of the opposing electrodes then computed from the corresponding sum and differences equations.

3. An apparatus for determing the ocular gaze point of regard and fixation duration, and the binocular convergence point of a viewer, comprising;

a headset;

a position and orientation sensor having a digital signal output, said sensor being connected to said headset so as to determine the position and orientation of said headset on said viewer's head;

a pair of goggles, having embedded electrodes for measuring electrooculographic potentials, connected to said headset and having an analog signal output;

an electronic device connected to the output of said goggles having an analog signal output that electronically represents spatially the electrooculographic measurements of the viewer's eye;

an electronic analog-to-digital converter, connected to said electronic device, having a digital signal output;

an electronic digital-to-analog converter and digital output device connected to said electronic device;

a digital computer connected to said position and orientation sensor, said analog-to-digital converter, and said digital-to-analog converter and digital output device, for computing the gaze points of regard and fixation durations, and the binocular convergence point of said viewer.

4. The device of claim 3 wherein said goggles further comprise:

a neoprene frame for said goggles such that said goggles fit around the eyes and provide a rigid base;

skin surface electrodes embedded in said neoprene frame, said electrodes being made from an electrically conducting nylon cloth fabric impregnated with silver particles;

said skin surface electrodes having a periocular arrangement, with two electrodes located horizontally at opposing temporal canthi sites, two electrodes mounted on a nasal site, two electrodes located vertically for each eye at opposing sites one above the eyebrow and the other below the eye at the infraobital foramen, and a common reference electrode; and the electrical leads from said electrodes arranged in a unipolar recording configuration with a common reference.

5. The device of claim 4 further comprising:

an array of isolation two-channel, differential-input, instrumentation preamplifiers each having one input connected to said electrode lead such that there is a one-to-one mapping between said amplifiers and said periocular arranged electrodes, and each having another input connected to said common reference;

an array of bias adjustment amplifiers to reduce the contributions from the direct current offset potential induced at the interface between said electrodes the skin surface, the inputs of said bias amplifiers being cascaded one-to-one with the outputs of said isolation amplifiers, and the DC bias offset voltages of said bias amplifiers being set by the analog outputs of said digital-to-analog converter;

an array of second stage programmable gain amplifiers having inputs cascaded one-to-one with the outputs of said bias adjustment amplifiers, the gain of said programmable gain amplifiers being set by the digital outputs of said digital output device;

an array of active filtering amplifiers for removing externally induced noise having inputs cascaded one-to-one with the outputs of said programmable gain amplifiers.

6. A method for computing the gaze point of regard and fixation duration for each eye, and the binocular convergence point for both eyes of a viewer comprising the steps of:

measuring the head related ocular angular directions;

computing the optical origin and axis, and the median axes from the head related ocular angular directions;

computing the viewing origin and axis for each eye from the corresponding optical origin and axis, and the median axes;

converting the viewing origin and axis for each eye to that of the viewer's workspace using the headset position and orientation sensor readings from a head tracker means;

classifying the viewing status of each eye as saccadic, fixation, or pursuit from the corresponding immediate eye movement history by utilizing automatic fixation and saccade classification schemes and a velocity based prediction scheme;

grouping local fixations into gaze points, and computing the gaze point of regard in the viewer's workspace and fixation duration from the corresponding viewing origin and axis, and an embedded memory table of the workspace geometry; and computing the binocular convergence point from the viewing origins and axes of both eyes for the viewer's workspace.

* * * * *